US006214316B1

(12) United States Patent
Dean

(10) Patent No.: US 6,214,316 B1
(45) **Date of Patent: *Apr. 10, 2001**

(54) SOMATOSTATIN ANALOGS

(75) Inventor: Richard T. Dean, Bedford, NH (US)

(73) Assignee: Diatide, Inc., Londonderry, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/420,865

(22) Filed: Oct. 19, 1999

Related U.S. Application Data

(63) Continuation-in-part of application No. 08/092,355, filed on Jul. 15, 1993, now Pat. No. 6,017,509.

(51) Int. Cl.$^7$ .......................... A61K 51/00; A61M 36/14

(52) U.S. Cl. ...................... 424/1.69; 424/1.11; 424/1.65; 424/1.81; 530/300; 530/311

(58) Field of Search ................................. 424/1.11, 1.65, 424/1.69, 1.81, 1.85; 530/300, 324–330, 333, 334, 338, 311, 317; 206/223, 569, 570

(56) References Cited

U.S. PATENT DOCUMENTS

| | | | | |
|---|---|---|---|---|
| 4,310,415 | | 1/1982 | Freidinger et al. . | |
| 4,486,415 | | 12/1984 | Freidinger . | |
| 4,650,787 | | 3/1987 | Schally et al. . | |
| 4,725,577 | | 2/1988 | Schally et al. . | |
| 5,443,815 | * | 8/1995 | Dean et al. | 424/1.69 |
| 5,932,189 | * | 8/1999 | Dean et al. | 424/1.69 |
| 5,955,426 | * | 9/1999 | Dean et al. | 514/11 |
| 6,017,509 | * | 1/2000 | Dean et al. | 424/1.69 |
| 6,051,206 | * | 4/2000 | Dean et al. | 424/1.69 |

FOREIGN PATENT DOCUMENTS

| | | |
|---|---|---|
| 0 143 307 | 6/1985 | (EP) . |
| 0 222 576 | 5/1987 | (EP) . |

* cited by examiner

*Primary Examiner*—Dameron Jones
(74) *Attorney, Agent, or Firm*—Patricia A. McDaniels; Kevin E. Noonan

(57) ABSTRACT

This invention relates to therapeutic reagents and peptides, including radiotherapeutic reagents and peptides, radiodiagnostic reagents and peptides, and methods for producing labeled radiodiagnostic agents. Specifically, the invention relates to cyclic peptide derivatives and analogs of somatostatin, and embodiments of such peptides radiolabeled with a radioisotope, as well as methods and kits for making, radiolabeling and using such peptides for radiodiagnostic and radiotherapeutic purposes. The invention specifically relates to cyclic peptide derivatives and analogues of somatostatin radiolabeled with technetium-99m and uses thereof as scintigraphic imaging agents. The invention also specifically relates to cyclic peptide derivatives and analogues of somatostatin radiolabeled with cytotoxic radioisotopes such as rhenium-186 ($^{186}$Re) and rhenium-188 ($^{188}$Re) for use as radiotherapeutic agents. Methods and kits for making, radiolabeling and using such peptides diagnostically and therapeutically in a mammalian body are also provided.

6 Claims, No Drawings

SEQUENCE LISTING

```
<160> NUMBER OF SEQ ID NOS: 1

<210> SEQ ID NO 1
<211> LENGTH: 14
<212> TYPE: PRT
<213> ORGANISM: Homo sapiens
<220> FEATURE:
<221> NAME/KEY: DISULFID
<222> LOCATION: (3)..(14)

<400> SEQUENCE: 1

Ala Gly Cys Lys Asn Phe Phe Trp Lys Thr Phe Thr Ser Cys
  1             5                   10
```

SOMATOSTATIN ANALOGS

This application is a continuation-in-part of U.S. patent application Ser. No. 08/092,355, filed Jul. 15, 1993 and now U.S. Pat. No. 6,017,509.

BACKGROUND OF THE INVENTION

This invention relates to therapeutic agents and peptides, radiotherapeutic agents and peptides, radiodiagnostic agents and peptides, and methods for producing such labeled radiodiagnostic and radiotherapeutic agents. Specifically, the invention relates to cyclic peptide derivatives and analogues of somatostatin, and embodiments of such peptides labeled with gamma-radiation emitting isotopes such as technetium-99m (Tc-99m), as well as methods and kits for making, radiolabeling and using such peptides to image sites in a mammalian body. The invention also relates to peptide derivatives and analogues of somatostatin labeled with cytotoxic radioisotopes such as rhenium-186 ($^{186}$Re) and rhenium-188 ($^{188}$Re), and methods and kits for making, radiolabeling and using such peptides therapeutically in a mammalian body.

Somatostatin is a tetradecapeptide that is endogenously produced by the hypothalamus and pancreas in humans and other mammals. The peptide has the formula:

Formula I

Ala-Gly-Cys-Lys-Asn-Phe-Phe-Trp-Lys-Thr-Phe-Thr-Ser-Cys (SEQ ID NO:1)

[Single letter abbreviations for amino acids can be found in G. Zubay, *Biochemistry* (2d ed.), 1988, (MacMillan Publishing: New York), p.33]. This peptide exerts a wide variety of biological effects in vivo. It is known to act physiologically on the central nervous system, the hypothalamus, the pancreas, and the gastrointestinal tract.

Somatostatin inhibits the release of insulin and glucagon from the pancreas, inhibits growth hormone release from the hypothalamus, and reduces gastric secretions. Thus, somatostatin has clinical and therapeutic applications for the alleviation of a number of ailments and diseases, both in humans and other animals. Native somatostatin is of limited utility, however, due to its short half-life in vivo, where it is rapidly degraded by peptidases. For this reason, somatostatin analogues having improved in vivo stability have been developed in the prior art.

Freidinger, U.S. Pat. No. 4,235,886 disclose cyclic hexapeptide somatostatin analogues useful in the treatment of a number of diseases in humans.

Coy and Murphy, U.S. Pat. No. 4,485,101 disclose synthetic dodecapeptide somatostatin analogues.

Freidinger, U.S. Pat. No. 4,611,054 disclose cyclic hexapeptide somatostatin analogues useful in the treatment of a number of diseases in humans.

Nutt, U.S. Pat. No. 4,612,366 disclose cyclic hexapeptide somatostatin analogues useful in the treatment of a number of diseases in humans.

Coy et al., U.S. Pat. No. 4,853,371 disclose synthetic octapeptide somatostatin analogues.

Coy and Murphy, U.S. Pat. No. 4,871,717 disclose synthetic heptapeptide somatostatin analogues.

Coy et al., U.S. Pat. No. 4,904,642 disclose synthetic octapeptide somatostatin analogues.

Taylor et al., U.S. Pat. No. 5,073,541 disclose a method of treating small cell lung cancer.

Brady, European Patent Application No. 83111747.8 discloses dicyclic hexapeptide somatostatin analogues useful in the treatment of a number of human diseases.

Bauer et al., European Patent Application No. 85810617.2 disclose somatostatin derivatives useful in the treatment of a number of human diseases.

Eck and Moreau, European Patent Application No. 90302760.5 disclose therapeutic octapeptide somatostatin analogues.

Coy and Murphy, International Patent Application Serial No. PCT/US90/07074 disclose somatostatin analogues for therapeutic uses.

Schally et al., European Patent Application Serial No. EPA 911048445.2 disclose cyclic peptides for therapeutic use.

Bodgen and Moreau, International Patent Application Serial No. PCT/US92/01027 disclose compositions and methods for treating proliferative skin disease.

Somatostatin exerts its effects by binding to specific receptors expressed at the cell surface of cells comprising the central nervous system, the hypothalamus, the pancreas, and the gastrointestinal tract. These high-affinity somatostatin binding sites have been found to be abundantly expressed at the cell surface of most endocrine-active tumors arising from these tissues. Expression of high-affinity binding sites for somatostatin is a marker for these tumor cells, and specific binding with somatostatin can be exploited to locate and identify tumor cells in vivo.

Methods for radiolabeling somatostatin analogues that have been modified so as to contain a tyrosine amino acid (Tyr or Y) are known in the prior art.

Albert et al., UK Patent Application 8927255.3 disclose radioimaging using somatostatin derivatives such as octreotide labeled with $^{123}$I.

Bakker et al., 1990, J. Nucl. Med. 31: 1501–1509 describe radioactive iodination of a somatostatin analog and its usefulness in detecting tumors in vivo.

Bakker et al., 1991, J. Nucl. Med. 32: 1184–1189 teach the usefulness of radiolabeled somatostatin for radioimaging in vivo.

Bomanji et al., 1992, J. Nucl. Med. 33: 1121–1124 describe the use of iodinated (Tyr-3) octreotide for imaging metastatic carcinoid tumors.

Alternatively, methods for radiolabeling somatostatin by covalently modifying the peptide to contain a radionuclide-chelating group have been disclosed in the prior art.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Albert et al., European Patent Application No. 92810381.1 disclose somatostatin peptides having amino-terminally linked chelators.

Faglia et al., 1991, J. Clin. Endocrinol. Metab. 73: 850–856 describe the detection of somatostatin receptors in patients.

Kwekkeboom et al., 1991, J. Nucl. Med. 32: 981 Abstract #305 relates to radiolabeling somatostatin analogues with $^{111}$In.

Albert et al., 1991, Abstract LM10, 12th American Peptide Symposium: 1991 describe uses for $^{111}$In-labeled diethylene-triaminopentaacetic acid-derivatized somatostatin analogues.

Krenning et al., 1992, J. Nucl. Med. 33: 652–658 describe clinical scintigraphy using [$^{111}$In][DTPA]octreotide.

These methods can be readily adapted to enable detection of tumor cells in vivo by radioimaging, based on the expression of high affinity binding sites for somatostatin on tumor cells. Radionuclides which emit gamma radiation can be readily detected by scintigraphy after injection into a human or an animal. A variety of radionuclides are known to be useful for radioimaging, including $^{67}$Ga, $^{68}$Ga, $^{99m}$Tc (Tc-99m), $^{111}$In, $^{123}$ or $^{125}$I. The sensitivity of imaging methods us radioactively-labeled peptides is much higher than other techniques known in the art, since the specific binding of the radioactive peptide concentrates the radioactive signal over the cells of interest, for example, tumor cells. This is particularly important for endocrine-active gastrointestinal tumors, which are usually small, slow-growing and difficult to detect by conventional methods. Labeling with technetium-99m (Tc-99m) is advantageous because the nuclear and radioactive properties of this isotope make it an ideal scintigraphic imaging agent. Tc-99m has a single photon energy of 140 keV and a radioactive half-life of about 6 hours, and is readily available from a $^{99}$Mo-$^{99m}$Tc generator. Other radionuclides have effective half-lives which are much longer (for example, $^{111}$In, which has a half-life of 60–70 h) or are toxic (for example, $^{125}$I). Although Tc-99m is an ideal radiolabeling reagent, it has not been widely used in the art prior to the present invention [see, for example, Lamberts, J. Nucl. Med. 32: 1189–1191 (1991)].

Somatostatin and radiolabeled somatostatin analogues can also be used therapeutically. For these applications, cytotoxic radioisotopes are advantageous, such as scandium-47, copper-67, gallium-72, yttrium-90, iodine-125, iodine-131, samarium-153, gadolinium-159, dysprosium-165, holmium-166, ytterbium-175, lutetium-177, rhenium-186, rhenium-188, astatine-211 and bismuth-212. The rhenium isotopes $^{186}$Re and $^{188}$Re are particularly advantageous.

The use of chelating agents for radiolabeling proteins are known in the prior art, and methods for labeling peptides Tc-99m are disclosed in commonly assigned U.S. Pat. Nos. 5,811,394; 5,225,180;5,443,815; 5,711,931; 5,780,007; 5,849,260; 5,508,020; 5,405,597; 5,225,525; 5,645,815; and 5,561,220 and in allowed U.S. patent application Ser. No. 08/361,864; and in International Applications PCT/US92/00757, PCT/US92/10716, PCT/US93/02320, PCT/US93/03687, PCT/US93/04794, PCT/US93/05372, and PCT/US93/06029, which are hereby incorporated by reference.

Fritzberg, U.S. Pat. No. 4,444,690 describes a series of technetium-chelating agents based on 2,3-bis(mercaptoacetamido)propanoate.

Gansow et al., U.S. Pat. No. 4,472,509 teach methods of manufacturing and purifying Tc-99m chelate-conjugated monoclonal antibodies.

Reno and Bottino, European Patent Application 87300426.1 disclose radiolabeling antibodies with Tc-99m.

Pak et al., European Patent Application No. WO 88/07382 disclose a method for labeling antibodies with Tc-99m.

Cox, International Patent Application No. PCT/US92/04559 discloses radiolabeled somatostatin derivatives containing two cysteine residues.

Rhodes, 1974, Sem. Nucl. Med. 4: 281–293 teach the labeling of human serum albumin with technetium-99m.

Khaw et al., 1982, J. Nucl. Med. 23: 1011–1019 disclose methods for labeling biologically active macromolecules with Tc-99m.

Byrne and Tolman, supra, disclose a bifunctional thiolactone chelating agent for coupling Tc-99m to biological molecules.

Cox et al., 1991, Abstract, 7th International Symposium on Radiopharmacology, p. 16, disclose the use of, Tc-99m-, $^{131}$I- and $^{111}$In-labeled somatostatin analogues in radiolocalization of endocrine tumors in vivo by scintigraphy.

Methods for directly labeling somatostatin, derivatives of somatostatin, analogues of somatostatin or peptides that bind to the somatostatin receptor and contain at least two cysteine residues that form a disulfide or wherein the disulfide is reduced to the sulfhydryl form, are disclosed in U.S. Pat. No. 5,225,180.

There remains a need for synthetic (to make routine manufacture practicable and to ease regulatory acceptance) somatostatin analogues having increased in vivo stability, to be used therapeutically, as scintigraphic agents when radiolabeled with Tc-99m or other detectable radioisotopes for use in imaging tumors in vivo, and as radiotherapeutic agents when radiolabeled with a cytotoxic radioisotope such as rhenium-188. Small synthetic somatostatin analogues are provided by this invention that specifically fulfill this need.

SUMMARY OF THE INVENTION

The present invention provides somatostatin analogues that are cyclic peptides for therapeutic applications, including radiotherapeutic applications, and diagnostic applications, including radiodiagnostic applications, in particular scintigraphic imaging applications. Distinct from native somatostatin and somatostatin analogues known in the prior art, the cyclic peptides of the invention are not comprised of a disulfide bond. The invention also provides cyclic peptide reagents comprised of the cyclic peptide somatostatin analogues of the invention, wherein such peptides are covalently linked to a radiolabel-binding moiety. The invention provides such cyclic peptides, cyclic peptide reagents and radiolabeled cyclic peptide reagents that are scintigraphic imaging agents, radiodiagnostic agents and radiotherapeutic agents. Scintigraphic imaging agents of the invention comprise cyclic peptide reagents radiolabeled with a radioisotope, preferably technetium-99m. Radiotherapeutic agents of the invention comprise cyclic peptide reagents radiolabeled with a cytotoxic radioisotope, preferably rhenium-186 or rhenium-188. Methods for making and using such cyclic peptides, cyclic peptide reagents and radiolabeled embodiments thereof are also provided.

The invention provides a cyclic peptide that is a somatostatin analogue as a composition of matter comprising a somatostatin-receptor binding peptide having the formula:

Formula II

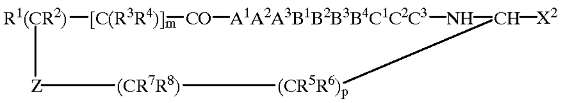

where $R^1$, $R^2$, $R^5$ and $R^6$ are each independently H, lower alkyl or substituted alkyl, aryl or substituted aryl; $R^3$ and $R^4$ are each independently H, lower alkyl or substituted alkyl, aryl or substituted aryl, or wherein either $R^3$ or $R^4$ is $X^1$; $A^1$ and $C^3$ are independently a bond or a D- or L-amino acid; $A^2$, $A^3$ and $C^1$ are each independently a bond or a lipophilic D- or L-amino acid; $B^1$ is D- or L-Phe or D- or L-Tyr or D- or L-2-naphthylalanine (Nal) or 2-aminoindan-2-carboxylic acid (Ain) or a substituted derivative thereof; $B^2$ is D- or L-Trp or a substituted derivative thereof; $B^3$ is D- or L-Lys or homolysine (Hly), 4-amino-cyclohexylalanine (Achxa), 4-aminomethylphenylalanine (Amf), S-(2-aminoethyl) cysteine (Aec), S-(3-aminopropyl)cysteine (Apc), O-(2-aminoethyl)serine (Aes), O-(3-aminopropyl)serine (Aps) or a substituted derivative thereof; $B^4$ is Thr, Ser, Val, Phe, Ile, Leu, 2-amino-isobutyric acid (Aib), 2-aminobutyric acid (Abu), norvaline (Nva), or norleucine (Nle); $C^2$ is a bond or D- or L-Thr, Ser, Val, Phe, Be, Abu, Nle, Leu, Nva, Nal or Aib or a substituted derivative thereof; $X^1$ is $N(R^{10})_2$, where each $R^{10}$ is independently hydrogen, lower alkyl or substituted lower alkyl, aryl or substituted aryl or a hydrophilic moiety of less than about 1500 daltons; $X^2$ is $—COOR^9$, $—CH_2OH$, $CH_2COOR^9$, or $—CON(R^9)_2$, where each $R^9$ is independently H, lower linear or cyclic alkyl or a substituted derivative thereof or a hydrophilic moiety of less than about 1500 daltons; and where m is 0,1,2 or 3 and p is 0, 1 or 2; $R^7$ and $R^8$ are independently H, lower alkyl or substituted lower alkyl, or either $R^7$ or $R^8$ are —COOH or $—CO.N(R^{10})_2$ or $—COOR^{12}$, or $R^7$ and $R^8$ together are an oxygen atom; $R^{12}$ is hydrogen, lower alkyl or substituted lower alkyl, aryl or substituted aryl; Z is a sulfur atom, an oxygen atom, $NR^{13}$, $NR^{13}NR^{13}$, $NR^{13}.CO.NR^{13}$, $SO_2$, $NR^{13}SO_2$ or the moiety (S=O); and further where $R^{13}$ is hydrogen, lower alkyl or substituted lower alkyl, aryl or substituted aryl; and where Z is $NR^{13}$, $R^7$ and $R^8$ are not together an oxygen. In a preferred embodiment, the $X^1$ moiety is an amino acid or a peptide sequence comprising 10 or fewer amino acids, or a monosaccharide or oligosaccharide comprising 10 or fewer saccharide units, or a poly(N-carboxyalkyl)amine or a polyoxy anion and the $x^2$ moiety is poly(N-carboxyalkyl) amine or a polyoxy-anion, or an amino acid or a peptide having an amino acid sequence of no more than 10 residues (including peptides wherein the carboxyl group of the carboxyl-terminal amino acid is reduced to an alcohol), or a monosaccharide or oligosaccharide comprising 10 or fewer saccharide units. In another preferred embodiment, $B^1$ is phenylalanine or tyrosine, $B^2$ is D-tryptophan, $B^3$ is lysine and $B^4$ is threonine or valine.

The invention also provides a cyclic peptide that is a somatostatin analogue as a composition of matter comprising a somatostatin-receptor binding peptide having the formula:

cyclo-$A^4$-$B^1B^2B^3B^4$-$C^4$- Formula III where $B^1$ is D- or L-Phe or D- or L-Tyr or D- or L-Nal or Ain or a substituted derivative thereof; $B^2$ is D- or L-Trp or a substituted derivative thereof; $B^3$ is D- or L-Lys or Hly, Achxa, Amf, Aec, Apc, Aes, Aps or a substituted derivative thereof; $B^4$ is Thr, Ser, Val, Phe, ile, Abu, Nle, Leu, Nva or Aib; $C^4$ is an L-amino acid comprising a side chain having a mercapto group; and $A^4$ is a lipophilic D-amino acid or a lipophilic L-(α-N-alkyl)amino acid or L-cysteine or L-proline or a substituted derivative thereof. This moiety is a cyclic peptide moiety, where the amino terminus of the $A^4$ residue is covalently linked with the carboxyl terminus of the $C^4$ residue. In a preferred embodiment, $B^1$ is phenylalanine or tyrosine, $B^2$ is D-tryptophan, $B^3$ is lysine and $B^4$ is threonine or valine.

The invention also provides a cyclic peptide reagent comprising a somatostatin-receptor binding peptide having the formula:

Formula II

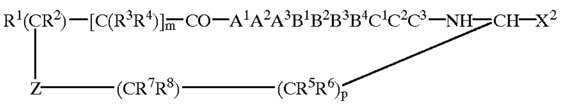

where $R^1$, $R^2$, $R^5$ and $R^6$ are each independently H, lower alkyl or substituted alkyl, aryl or substituted aryl; $R^3$ and $R^4$ are each independently H, lower alkyl or substituted alkyl, aryl or substituted aryl, or wherein either $R^3$ or $R^4$ is $X^1$; $A^1$ and $C^3$are independently a bond or a D- or L-amino acid; $A^2$, $A^3$ and $C^1$ are each independently a bond or a lipophilic D- or L-amino acid; $B^1$ is D- or L-Phe or D- or L-Tyr or D- or L-2-naphthylalanine (Nal) or 2-aminoindan-2-carboxylic acid (Ain) or a substituted derivative thereof; $B^2$ is D- or L-Trp or a substituted derivative thereof; $B^3$ is D- or L-Lys or homolysine (Hly), 4-amino-cyclohexylalanine (Achxa), 4-aminomethylphenylalanine (Amf), S-(2-aminoethyl) cysteine (Aec), S-(3-aminopropyl)cysteine (Apc), O-(2-aminoethyl)serine (Aes), O-(3-aminopropyl)serine (Aps) or a substituted derivative thereof; $B^4$ is Thr, Ser, Val, Phe, Ile, Leu, 2-amino-isobutyric acid (Aib), 2-amninobutyric acid (Abu), norvaline (Nva), or norleucine (Nle); $C^2$ is a bond or D- or L-Thr, Ser, Val, Phe, Ile, Abu, Nle, Leu, Nva, Nal or Aib or a substituted derivative thereof; $X^1$ is $N(R^{10})_2$, where each $R^{10}$ is independently hydrogen, lower alkyl or substituted lower alkyl, aryl or substituted aryl or substituted with a hydrophilic moiety of less than about 1500 daltons; $X^2$ is $—COOR^9$, $—CH_2OH$, $CH_2COOR^9$, or $—CON(R^9)_2$, where each $R^9$ is independently H, lower linear or cyclic alkyl or a substituted derivative thereof or substituted with a hydrophilic moiety of less than about 1500 daltons; and where m is 0,1,2 or 3 and p is 0, 1 or 2; $R^7$ and $R^8$ are independently H, lower alkyl or substituted lower alkyl, or either $R^7$ or $R^8$ are —COOH or $—CO.N(R^{10})_2$ or $—COOR^{12}$, or $R^7$ and $R^8$ together are an oxygen atom; $R^{12}$ is hydrogen, lower alkyl or substituted lower alkyl, aryl or substituted aryl; Z is a bond, a sulfur atom, an oxygen atom, $NR^{13}$, $NR^{13}NR^{13}$, $NR^{13}.CO.NR^{13}$, $SO_2$, $NR^{13}SO_2$ or the moiety (S=O); and further where $R^{13}$ is hydrogen, lower alkyl or substituted lower alkyl, aryl or substituted aryl; and where Z is $NR^{13}$, $R^7$ and $R^8$ are not together an oxygen. In a preferred embodiment, the $X^1$ moiety is an amino acid or a peptide sequence comprising 10 or fewer amino acids, or a monosaccharide or oligosaccharide comprising 10 or fewer saccharide units, or a poly(N-carboxyalkyl)amine or a polyoxy anion and the $X^2$ moiety is poly(N-carboxyalkyl)amine or a polyoxy-anion, or an amino acid or a peptide having an amino acid sequence of no more than 10 residues (including peptides wherein the carboxyl group of the carboxyl-terminal amino acid is reduced to an alcohol), or a monosaccharide or oligosaccharide comprising 10 or fewer saccharide units. In another preferred embodiment, $B^1$ is phenylalanine or tyrosine, $B^2$ is D-tryptophan, $B^3$ is lysine and $B^4$ is threonine or valine.

The invention also provides a cyclic peptide that is a somatostatin analogue as a composition of matter comprising a somatostatin-receptor binding peptide having the formula:

cyclo-$A^4$-$B^1B^2B^3B^4$-$C^4$- Formula III where $B^1$ is D- or L-Phe or D- or L-Tyr or D- or L-Nal or Ain or a substituted derivative thereof; $B^2$ is D- or L-Trp or a substituted derivative thereof; $B^3$ is D- or L-Lys or Hly, Achxa, Amf, Aec, Apc, Aes, Aps or a substituted derivative thereof; $B^4$ is Thr, Ser, Val, Phe, Ile, Abu, Nle, Leu, Nva or Aib; $C^4$ is an L-amino acid; and $A^4$ is a lipophilic D-amino acid or a lipophilic L-(α-N-alkyl)amino acid or L-cysteine or L-proline or a substituted derivative thereof; . This moiety is a cyclic peptide moiety, where the amino terminus of the $A^4$ residue is covalently linked with the carboxyl terminus of the $C^4$ residue. In a preferred embodiment, $B^1$ is phenylalanine or tyrosine, $B^2$ is D-tryptophan, $B^3$ is lysine and $B^4$ is threonine or valine; and wherein the cyclic peptide is covalently linked to a radiolabel-binding moiety, wherein the radiolabel-binding moiety is not covalently linked to the moieties $B^1$, $B^2$, $B^3$, $B^4$ or $A^4$ of the peptide.

The invention also provides scintigraphic imaging agents comprising the cyclic peptide reagents of the invention wherein the radiolabel-binding moiety is stably complexed with a radioisotope. In one such embodiment is provided a scintigraphic imaging agent wherein the somatostatin analogue, cyclic peptide reagents of the invention are radiolabeled with technetium-99m. In other embodiments of the scintigraphic imaging agents of the invention the radioisotope is indium-111 or gallium-68. In still other embodiments, the scintigraphic imaging agents of the invention are cyclic peptides that are radiolabeled with iodine-123 or iodine-125.

The invention also provides radiotherapeutic agents that are the cyclic peptide reagents of the invention radiolabeled with a cytotoxic radioisotope that is selected from the group consisting of scandium-47, copper-67, gallium-72, yttrium-90, samarium-153, gadolinium-159, dysprosium-165, holmium-166, ytterbium-175, lutetium-177, rhenium-186, rhenium-188, and bismuth-212. In preferred embodiments, the radioisotope is rhenium-186 or rhenium-188. In additional preferred embodiments, the cyclic peptides of the invention are radiolabeled with iodine-125, iodine-131 or astatine-211.

The invention further provides therapeutic agents comprising the cyclic peptide reagents of the invention, optionally wherein the reagents form a complex with a non-radioactive metal, preferably rhenium. In this aspect of the invention, the cyclic peptide somatostatin analogues have increased in vivo stability compared with native somatostatin. Combination embodiments, wherein such a complex is also radiolabeled, either directly or via a radiolabel-binding moiety, are also provided by the invention and are within its scope.

The somatostatin analogues of the invention are therapeutically useful in the alleviation of diseases or other ailments in humans or other animals.

The invention also provides pharmaceutical compositions comprising the somatostatin receptor-binding peptides of the invention in a pharmaceutically acceptable carrier.

The invention also provides a method for alleviating somatostatin-related diseases in animals, preferably humans, comprising administering a therapeutically effective amount of the somatostatin analogues of the invention to the animal. In preferred embodiments, the amount of the somatostatin analogue administered is from about 0.1 to about 50 mg/kg body weight/day.

Another aspect of the present invention provides reagents for preparing scintigraphic imaging agents, each reagent comprising a peptide that is somatostatin analogue and is covalently linked to a radiolabel-binding moiety.

It is an advantage of the somatostatin analogues provided by this invention that the non-disulfide cyclic linkage contained therein is stable under the conditions of radiolabeling the covalently linked radiolabel-binding moiety. In contrast, for example, Tc-99m conjugation to a Tc-99m binding moiety covalently linked to native somatostatin, or to a somatostatin analogue having a disulfide bond, can result in reduction of the disulfide accompanied by a loss of biological activity. Such loss of biological activity can also occur in vivo using native somatostatin, or to any somatostatin analogue having a disulfide bond. The present invention is not subject to similar losses in biological activity in vivo because the non-disulfide cyclic linkages in each of the somatostatin analogues of the invention comprise stable covalent bonds. It is another advantage of the somatostatin analogues provided by this invention that the cyclic covalent linkage acts to protect the peptide from degradation by exopeptidases. Further, the cyclic structure confers a degree of conformational rigidity to the peptide that can act to enhance binding of the peptide to its biological target (i.e., the somatostatin receptor).

A first aspect of the reagents provided by the invention for preparing radiolabeled agents are reagents that are each comprised of a cyclic peptide that is a somatostatin analogue that is covalently linked to a radiolabel-binding moiety having the formula:

$C(pgp)^S$-(aa)-$C(pgp)^S$ where $(pgp)^S$ is hydrogen or a thiol protecting group and (aa) is an amino acid. In a preferred embodiment, the amino acid is glycine. In another preferred embodiment, the agent is a scintigraphic imaging agent. In yet another preferred embodiment, the agent is a radiotherapeutic agent.

In a second embodiment, the invention provides cyclic peptide reagents capable of being radiolabeled to form radiodiagnostic and radiotherapeutic agents, each comprising a somatostatin analogue that is covalently linked to a radiolabel-binding moiety comprising a single thiol moiety of formula:

$A-CZ(B)-[C(R'R'')]_n-X$ wherein A is H, HOOC, $H_2NOC$, (peptide)-NHOC, (peptide)-OOC or R''''; B is H, SH or —NHR''', —N(R''')-

(peptide) or R''''; Z is H or R''''; X is SH or —NHR''', —N(R''')-(peptide) or R''''; R', R'', R''' and R'''' are independently H or straight or branched chain or cyclic lower alkyl; n is 0, 1 or 2; and: (1) where B is —NHR''' or —N(R''')-(peptide), X is SH and n is 1 or 2; (2) where X is —NHR'''or —N(R''')-(peptide), B is SH and n is 1 or 2; (3) where B is H or R'''', A is HOOC, $H_2NOC$, (peptide)-NHOC, (peptide)-OOC, X is SH and n is 0 or 1; (4) where A is H or R'''', then where B is SH, X is —NHR''' or —N(R''')-(peptide) and where X is SH, B is —NHR''' or —N(R''')-(peptide); (5) where X is H or R'''', A is HOOC, $H_2NOC$, (peptide)-NHOC, (peptide)-OOC and B is SH; (6) where Z is methyl, X is methyl, A is HOOC, $H_2NOC$, (peptide)-NHOC, (peptide)-OOC and B is SH and n is 0; and wherein the thiol moiety is in the reduced form. In a preferred embodiment, the agent is a scintigraphic imaging agent. In yet another preferred embodiment, the agent is a radiotherapeutic agent.

In another embodiment, the invention provides cyclic peptide reagents capable of being radiolabeled with a radioisotope to form radiodiagnostic and radiotherapeutic agents, each comprising a somatostatin analogue that is covalently linked to a radiolabel-binding moiety of formula:

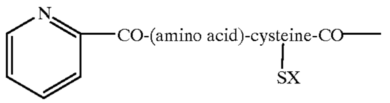

[for purposes of this invention, radiolabel-binding moieties having this structure will be referred to as picolinic acid (Pic)-based moieties] or

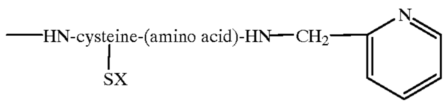

wherein X is H or a protecting group; (amino acid) is any amino acid and the radiolabel-binding moiety is covalently linked to the peptide. For purposes of this invention, radiolabel-binding moieties having this structure will be referred to as picolylamine (Pica)-based moieties. In a preferred embodiment, the amino acid is glycine and X is an acetamidomethyl protecting group. In another preferred embodiment, the agent is a scintigraphic imaging agent. In yet another preferred embodiment, the agent is a radiotherapeutic agent.

Yet another embodiment of the invention provides cyclic peptide reagents capable of being radiolabeled with a radioisotope for imaging sites within a mammalian body or for radiotherapeutic purposes, each comprising a somatostatin analogue that is covalently linked to a radiolabel-binding moiety that is a bisamino-bisthiol radiolabel-binding moiety. The bisamino bisthiol radiolabel-binding moiety in this embodiment of the invention has the formula:

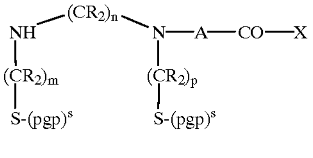

wherein each R can be independently H, $CH_3$ or $C_2H_5$; each $(pgp)^S$ can be independently a thiol protecting group or H; m, n and p are independently 2 or 3; A is linear or cyclic lower alkyl, aryl, heterocyclyl, combinations or substituted derivatives thereof; and X is peptide; or

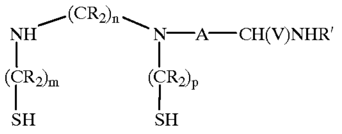

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is peptide. For purposes of this invention, radiolabel-binding moieties having these structures will be referred to as "BAT" moieties. In a preferred embodiment, the agent is a scintigraphic imaging agent. In yet another preferred embodiment, the agent is a radiotherapeutic agent.

This invention provides methods for preparing peptide reagents of the invention by chemical synthesis in vitro. In a preferred embodiment, cyclic peptides are synthesized by solid phase peptide synthesis.

This invention provides reagents for preparing a radiolabeled somatostatin receptor-binding agent comprising the somatostatin receptor-binding cyclic peptides of the invention covalently linked to a radiolabel-binding moiety. In a preferred embodiment, the reagent is radioactively labeled with Tc-99m. In another preferred embodiment, the reagent is radioactively labeled with $^{186}Re$ or $^{188}Re$.

The invention also comprises agents that are complexes of the cyclic peptide reagents of the invention with a radioisotope, as well as methods for radiolabeling the peptide reagents of the invention. For example, scintigraphic imaging agents provided by the invention comprise Tc-99m labeled complexes formed by reacting the peptide reagents of the invention with Tc-99m in the presence of a reducing agent. Preferred reducing agents include but are not limited to dithionite ion, stannous ion and ferrous ion. Such Tc-99m complexes of the invention are also formed by labeling the peptide reagents of the invention with Tc-99m by ligand exchange of a prereduced Tc--99m complex as provided herein.

The invention also provides kits for preparing radiolabeled somatostatin analogue cyclic peptides from the peptide reagents of the invention. Kits for radiolabeling the peptide reagents of the invention are comprised of a sealed vial containing a predetermined quantity of a peptide reagent of the invention and a sufficient amount of reducing agent to radiolabel the peptide. In a preferred embodiment, the radiolabeled somatostatin analogue is a scintigraphic imaging agent. Also preferred is radiolabeling the peptide reagents of the invention with Tc-99m. Kits for preparing radiotherapeutic agents are also provided, wherein the preferred radioisotopes are rhenium-186 and rhenium-188.

This invention provides methods for using the radiolabeled peptide reagents of the invention diagnostically and therapeutically. In one embodiment of the invention, methods are provided for using scintigraphic imaging agents that are Tc-99m labeled peptide reagents for imaging sites within a mammalian body by obtaining in vivo gamma scintigraphic images. These methods comprise administering an effective diagnostic amount of radiolabeled peptide reagents of the invention and detecting the gamma radiation emitted by the radiolabel localized at the site within the mammalian body.

The invention also provides methods for alleviating somatostatin-related diseases in animals, preferably humans, comprising administering a therapeutically effective amount of the radiolabeled somatostatin-binding peptide reagents of the invention to the animal. In preferred embodiments, the reagent is radioactively labeled with $^{186}$Re or $^{188}$Re.

The cyclic peptides and cyclic peptide reagents of the invention may also be comprised of a polyvalent linking moiety. Polyvalent linking moieties of the invention are comprised of at least 2 identical linker functional groups capable of covalently bonding to somatostatin analogue cyclic peptides or radiolabel-binding moieties. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl)benzoic acid (DMBA), N-[2-(N'N'-bis(2-succinimidoethyl)aminoethyl)]-$N^6$,$N^9$-bis(2-methyl-2-mercaptopropyl)-6,9-diazanonanamide (BAT-BS), tris(succinimidylethyl)amine (TSEA), bis-succinimidohexane (BSH), 4-(O-$CH_2$CO-Gly-Gly-Cys.amide)-2-methylpropiophenone (ETAC) or a derivative thereof.

Specific preferred embodiments of the present invention will become evident from the following more detailed description of certain preferred embodiments and the claims.

DETAILED DESCRIPTION OF THE INVENTION

The present invention provides cyclic peptides that are somatostatin analogues and that are not comprised of a disulfide bond. Such somatostatin analogues thereby possess increased in vivo stability compared with native somatostatin. These cyclic peptides are themselves therapeutic agents for alleviating diseases and other ailments in animals including humans.

Also provided by the invention are cyclic peptides that may be radioiodinated or radioastatinated and which are thereby useful in radiotherapeutic and radiodiagnostic applications.

Another embodiment of these cyclic peptides that is provided by this invention are cyclic peptide reagents wherein the cyclic peptides of the invention are covalently linked to a radiolabel-binding moiety. Such cyclic peptide reagents are capable of being radiolabeled to provide radiodiagnostic or radiotherapeutic agents. One example of a radiodiagnostic application using the radiolabeled agents of the invention is scintigraphic imaging, wherein the location and extent of somatostatin receptor-bearing tumors may be determined. The cyclic peptide reagents of the invention can also advantageously be radiolabeled with cytotoxic radioisotopes such as rhenium-186 or rhenium-188 for radiotherapeutic uses. The cyclic peptide reagents of the invention are also useful in preparing complexes with non-radioactive metals, said complexes being useful therapeutically.

The invention provides a method for using the somatostatin analogues of the invention to alleviate diseases or other ailments in animals, preferably humans. These diseases and ailments include but are not limited to diabetes and diabetes-related retinopathy, cirrhosis of the liver and hepatitis infection, bleeding ulcers and other gastrointestinal bleeding, pancreatitis, central nervous system disorders, endocrine disorders, Alzheimer's disease, acromegaly and other diseases and disorders related to the production of inappropriate levels of growth hormone in vivo, and cancer, particularly those cancers whose growth is dependent or influenced by growth hormone production. Dosages of the somatostatin analogues provided by the invention may be the same as those dosages of native somatostatin routinely used for treatment of the above or other diseases, or less of the compounds of the invention may be administered due to their longer in vivo half-life.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides may also be used in the practice of the invention as disclosed herein.

The term scintigraphic imaging agent as used herein is meant to encompass a radiolabeled agent capable of being detected with a radioactivity detecting means (including but not limited to a gamma-camera, a Geiger-Muller counter and a scintillation detector probe).

Radiotherapeutic embodiments of the invention, on the other hand, are advantageously labeled with a cytotoxic radioisotope, including but not limited to scandium-47, copper-67, gallium-72, yttrium-90, iodine-125, iodine-131, samarium-153, gadolinium-159, dysprosium-165, holmium-166, ytterbium-175, lutetium-177, rhenium-186, rhenium-188, astatine-211 and bismuth-212, most preferably $^{186}$Re or $^{188}$Re. Such embodiments are useful in the treatment of somatostatin-related diseases or other ailments in animals, preferably humans, including but not limited to cancer and other diseases characterized by the growth of malignant or benign tumors capable of binding somatostatin or somatostatin analogues via the expression of somatostatin receptors on the cell surface of cells comprising such tumors.

In the radiolabel-binding moieties and cyclic peptides covalently linked to such moieties that contain a thiol covalently linked to a thiol protecting groups [$(pgp)^S$] provided by the invention, the thiol-protecting groups may be the same or different and may be but are not limited to:

—$CH_2$-aryl (aryl is phenyl or alkyl or alkyloxy substituted phenyl);

—CH-$(aryl)_2$, (aryl is phenyl or alkyl or alkyloxy substituted phenyl);

—C-$(aryl)_3$, (aryl is phenyl or alkyl or alkyloxy substituted phenyl);

—$CH_2$-(4-methoxyphenyl);

—CH-(4-pyridyl)$(phenyl)_2$;

—$C(CH_3)_3$

-9-phenylfluorenyl;

—$CH_2NHCOR$ (R is unsubstituted or substituted alkyl or aryl);

—$CH_2$—NHCOOR (R is unsubstituted or substituted alkyl or aryl);

—CONHR (R is unsubstituted or substituted alkyl or aryl);

—$CH_2$—S—$CH_2$-phenyl

Preferred protecting groups have the formula —$CH_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each somatostatin receptor-binding cyclic peptide-containing embodiment of the invention is comprised of a sequence of amino acids. The term amino acid as used in this invention is intended to include all L- and D-amino acids, naturally occurring and otherwise. Reagents comprising somatostatin receptor-binding peptides provided by the invention include but are not limited to the following illustrative examples of the peptide embodiments of the invention:

cyclo.$(N-CH_3)$F.YW$_D$KV.Hcy
$CH_2CO$.FYW$_D$KTFC.amide
$CH_2CO$.FFW$_D$KTF.Hhc.amide
cyclo.CYW$_D$KVC
$CH_2CO$.FFW$_D$KTFC.amide
cyclo.$(N-CH_3)$F.YW$_D$KV.K.(BAT)
cyclo.$(N-CH_3)$F.YW$_D$KV.Hcy($CH_2CO$.K(ε-K)GC.amide)
cyclo.$(N-CH_3)$F.YW$_D$KV.Hcy($CH_2CO$.C$_{Acm}$GC$_{Acm}$.amide)
cyclo.$(N-CH_3)$F.YW$_D$KV.Hcy($CH_2CO$.CGC.amide)
cyclo.$(N-CH_3)$F.YW$_D$KV.Hcy($CH_2CO$.CGC)
$CH_2CO$.FFW$_D$KTFC.[BAM]
cyclo.$(N-CH_3)$F.YW$_D$KV.Hcy($CH_2CO$.(ε-K)GC.amide)
cyclo.$(N-CH_3)$F.YW$_D$KV.Hcy($CH_2CO$.GGC.amide)
cyclo.$(N-CH_3)$F.YW$_D$KV.E.(BAM)
$CH_2CO$.NFFW$_D$KTFTC
$CH_2CO$.FFW$_D$KTFC
$CH_2CO$.FFW$_D$KTFC(ε-K)GC.amide
$CH_2CO$.FFW$_D$KTFCC$_{Acm}$GC$_{Acm}$.amide
$CH_2CO$.FFW$_D$KTF.Hcy
$CH_2CO$.YW$_D$KTC
$CH_2CO$.YW$_D$KT.Hcy.amide
cyclo.$(N-CH_3)$F.YW$_D$KV.Hcy
$CH_2CO$.YW$_D$KT.Hhc.T($CH_2OH$)
$CH_2CO$.YW$_D$KTCTGGC$_{Mob}$.amide
$CH_2CO$.YW$_D$KT.Hhc
D-PHENYL-$CH_2$,$CH_2$ CO.YW$_D$KTC
$CH_2CO$.FW$_D$KT.Pen
$CH_2CO$.FW$_D$KTHcy.amide
$CH_2CO$.YW$_D$KTCT
$CH_2CO$.YW$_D$KTCT($CH_2OH$)
$CH_2CO$.YW$_D$KTCTC$_{Acm}$GC$_{Acm}$.amide
$CH_2CO$.FW$_D$KTHcy
$CH_2CO$.YW$_D$KTC.amide where the above structures, represented by single-letter amino acid sequence code correspond to the following three-letter amino acid sequence code:

| Structures Depicted by Single-Letter Code | Structures Depicted by Three-Letter Code |
|---|---|
| $CH_2CO.YW_DKT.Hhc$ | 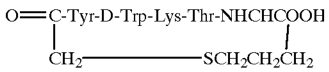 |
| D-PHENYL-$CH_2CH_2CO.YW_DKTC$ | 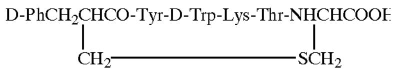 |
| $CH_2CO.FW_DKT.Pen$ | 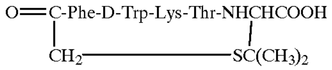 |
| $CH_2CO.FW_DKTHcy$.amide | 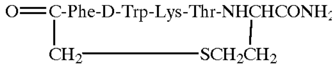 |
| $CH_2CO.YW_DKTCT$ | 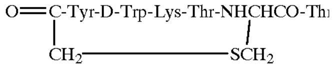 |
| $CH_2CO.YW_DKTCT(CH_2OH)$ | 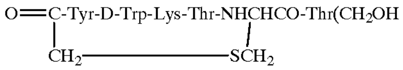 |
| $CH_2CO.YW_DKTCTC_{Acm}GC_{Acm}$.amide | 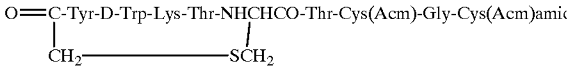 |
| $CH_2CO.FW_DKTHcy$ | 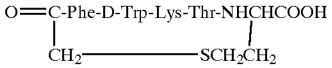 |
| $CH_2CO.YW_DKTC$.amide | 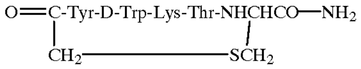 |
| cyclo.$(N—CH_3)F.YW_DKV.Hcy$ | cyclo.$(N—CH_3)$Phe—Tyr-D-Trp—Lys—Val—Hcy |
| $CH_2CO.FYW_DKTFC$.amide | 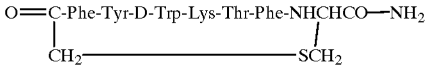 |

-continued

| Structures Depicted by Single-Letter Code | Structures Depicted by Three-Letter Code |
|---|---|
| $CH_2CO.FFW_DKTF.Hhc$.amide | 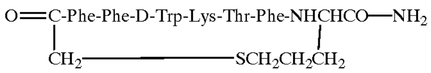 |
| cyclo.$CYW_DKVC$ | cyclo Cys—Tyr-D-Trp—Lys—Val—Cys (cyclic peptide, not disulfide) |
| $CH_2CO.FFW_DKTFC$.amide | 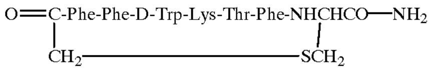 |
| cyclo.(N—$CH_3$)F.$YW_DKV$.K.(BAT) | cyclo.(N—$CH_3$)Phe—Tyr-D-Trp—Lys—Val—Lys(BAT) |
| cyclo.(N—$CH_3$)F.$YW_DKV$.Hcy($CH_2$CO.K(ε-K)GC.amide) | cyclo.(N—$CH_3$)Phe—Tyr-D-Trp—Lys—Val—Hcy($CH_2$CO—Lys(ε-Lys)—Gly—Cys-amide) |
| cyclo.(N—$CH_3$)F.$YW_DKV$.Hcy($CH_2CO.C_{Acm}GC_{Acm}$.amide) | cyclo.(N—$CH_3$)Phe—Tyr-D-Trp—Lys—Val—Hcy($CH_2$CO—Cys(Acm)—Gly—Cys(Acm)-amide) |
| cyclo.(N—$CH_3$)F.$YW_DKV$.Hcy($CH_2$CO.CGC.amide) | cyclo.(N—$CH_3$)Phe—Tyr-D-Trp—Lys—Val—Hcy($CH_2$CO—Cys—Gly—Cys-amide) |
| cyclo.(N—$CH_3$)F.$YW_DKV$.Hcy($CH_2$CO.CGC) | cyclo.(N—$CH_3$)Phe—Tyr-D-Trp—Lys—Val—Hcy($CH_2$CO—Cys—Gly—Cys) |
| $CH_2CO.FFW_DKTFC$.(BAM) | 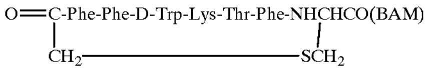 |
| cyclo.(N—$CH_3$)F.$YW_DKV$.Hcy($CH_2$CO.(ε-K)GC.amide) | cyclo.(N—$CH_3$)Phe—Tyr-D-Trp—Lys—Val—Hcy($CH_2$CO—(ε-Lys)—Gly—Cys-amide) |
| cyclo.(N—$CH_3$)F.$YW_DKV$.Hcy($CH_2$CO.GGC.amide) | cyclo.(N—$CH_3$)Phe—Tyr-D-Trp—Lys—Val—Hcy($CH_2$CO—Gly—Gly—Cys-amide) |
| cyclo.(N—$CH_3$)F.$YW_DKV$.E.(BAM) | cyclo.(N—$CH_3$)Phe—Tyr-D-Trp—Lys—Val—Glu(BAM) |
| $CH_2CO.NFFW_DKTFTC$ | 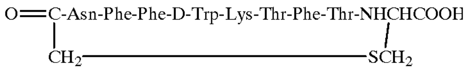 |
| $CH_2CO.FFW_DKTFC$ | 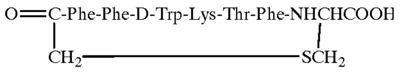 |

-continued
| Structures Depicted by Single-Letter Code | Structures Depicted by Three-Letter Code |
|---|---|
| $CH_2$CO.FFW$_D$KTFC(ε-K)GC.amide | 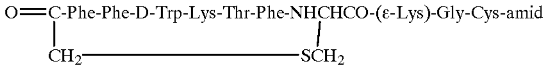 |
| $CH_2$CO.FFW$_D$KTFCC$_{Acm}$GC$_{Acm}$.amide | 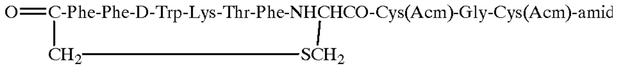 |
| $CH_2$CO.FFW$_D$KTF.Hcy | 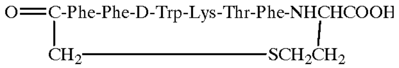 |
| $CH_2$CO.YW$_D$KTC | 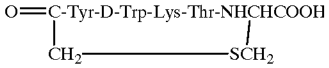 |
| $CH_2$CO.YW$_D$KT.Hcy.amide | 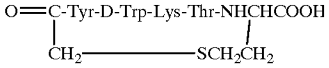 |
| $CH_2$CO.YW$_D$KT.Hhc.T($CH_2$OH) | 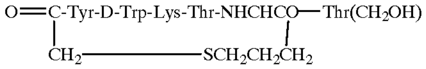 |
| $CH_2$CO.YW$_D$KTCTGGC$_{Mob}$.amide | 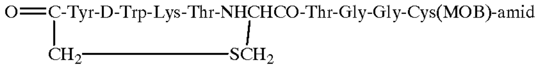 |

As used herein, the following amino acids and amino acid analogues are intended to be represented by the following abbreviations: Ac is an acetyl group; ma is mercaptoacetic acid group; Aca is 6-aminocaproic acid; Hcy is homocysteine; Hhc is homohomocysteine, which is (3-mercaptopropyl)glycine; Pen is penicillamine; Mob is the sulfhydryl protecting group 4-methoxybenzyl; Acm is the sulfhydryl protecting group acetamidomethyl; Aib is aminoisobutyric acid; Nal is 2-naphthylalanine; Ain is 2-aminoindan-2-carboxylic acid; Hly is homolysine; Achxa is 4-amino-cyclohexylalanine; Amf is 4-aminomethylphenylalanine; Aec is S-(2-aminoethyl) cysteine; Apc is S-(3-aminopropyl)cysteine; Aes is O-(2-aminoethyl)serine; Aps is O-(3-aminopropyl)serine; Abu is 2-aminobutyric acid; Nva is norvaline; $F_D$ is D-phenylalahine; $W_D$ is D-tryptophan; $Y_D$ is D-tyrosine; Cpa is L-(4-chlorophenyl)alanine; Thp is 4-amino-tetrahydrothiopyran-4-carboxylic acid; D-Nal is D-2-naphthylalanine; Dpg is dipropylglycine; and Nle is norleucine. For the purposes of this invention, the naturally-occurring amino acids are characterized as lipophilic (alanine, isoleucine, leucine, methionine, phenylalanine, tyrosine, proline, tryptophan and valine, as well as S-alkylated derivatives of cysteine), hydrophilic (asparagine, glutamine, threonine, serine), acidic (glutamic acid and aspartic acid), basic (arginine, histidine and lysine). $T(CH_{2\,OH})$ represents a threoninol residue, wherein the carboxyl group of the amino acid is reduced to a primary alcohol, incorporated into the peptide using the procedure of Neugebauer et al. (1990, *Peptides: Proceedings of the 11th American Peptide Symposium,* pp. 1020–21). ε-K is intended to represent a covalent linkage via the ε-amino group on the sidechain of a lysine residue. Pic is picolinoyl (pyridine-2-carbonyl); Pica is picolylamine (2-(aminomethyl)pyridine); [BAT] represents $N^6$,$N^9$-bis(2-mercapto-2-methylpropyl)-6,9-diazanonanoic acid; K.(BAT) and Lys.(BAT) represent the amino acid lysine, acylated at the ε-amino group on the amino acid sidechain to [BAT]; [BAM] is ($N^1$,$N^4$-bis(2-mercapto-2-methylpropyl)-1,4,10-triazadecane; E.(BAM) and Glu.(BAM) represent the amino acid glutamic acid having a γ-amide linkage between the sidechain carboxylic acid group of glutamic acid and a [BAM]-derived primary amino group; [BAT-BM] is N-[2-(N',N'-bis(2-maleimidoethyl) aminoethyl]-$N^9$-(t-butoxycarbonyl)-$N^6$,$N^9$-bis(2-methyl-2-triphenylmethylthiopropyl)-6,9-diazanonanamide; [BAT-BS] is N-[2-(N',N'-bis(2-succinimidoethyl)aminoethyl]-$N^6$, $N^9$-bis(2-mercapto-2-methylpropyl)-6,9-diazanonanamide; [BMME] is bis-maleimidomethylether; [BSME] is bis-succinimidomethylether; and [DTPA] is diethylenetriamine-pentaacetic acid. Hcy(alkyl group) is homocysteine, S-alkylated with the group in parenthesis.

The convention used herein of representing by underlining a covalent bond between atoms and groups of atoms, such as the amino terminus and carboxyl terminus resulting in the cyclic peptides of the invention, or similar representations of covalent bonding between the sidechain sulfur atom of a cysteine residue or derivative thereof and an amino terminal acyl group or other residue will also be understood by those with skill in the art. The use of the term "cyclo" herein is intended to indicate that the peptide is cyclized by formation of a covalent bond between the atoms of the amino terminal substituted or unsubstituted amino group and the carboxyl terminus of the peptide.

For the purposes of this invention the term "poly(N-carboxyalkyl)amine" in intended to describe a series of compounds exemplified by nitrilotriacetic acid, iminodiacetic acid, ethylenediaminetetraacetic acid (EDTA) and DTPA.

For the purposes of this invention the term "polyoxyanion" is intended to encompass sulfates, phosphates, sulfonates, phosphonates like compounds.

Somatostatin analogue peptides of the present invention can be chemically synthesized in vitro. Peptides of the present invention can generally advantageously be prepared on a peptide synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

Radiolabel binding moieties of the invention may be introduced into the target somatostatin analogue peptides during peptide synthesis. For embodiments comprising picolinic acid [(Pic-); e.g., Pic-Gly-Cys(protecting group)-], the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any appropriate position in the peptide chain. This sequence is particularly advantageous as it affords an easy mode of incorporation into the target somatostatin analogue peptide.

Similarly, the picolylaamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

This invention also provides small synthetic peptides that are somatostatin analogues and incorporate bisamine bisthiol (BAT) chelators that may be labeled with Tc-99m.

This invention provides for the incorporation of these chelators into virtually any position in the peptide, via covalently linkage to any appropriate functional group of the peptide, except that the chelating moieties of the invention are not covalently linked to functional groups comprising the amino acid side chains of the amino acids $B^1$, $B^2$, $B^3$ or $B^4$.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled peptides is provided. An appropriate amount of the peptide reagent is introduced into a vial containing a reducing agent, such as stannous chloride, in an amount sufficient to label the peptide with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Tc-99m labeled imaging reagents according to the present invention may be prepared by the addition of an appropriate amount of Tc-99m or Tc-99m complex into the vials and reaction under conditions described in Example 2 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per niL.

The imaging reagents provided by the present invention can be used for visualizing organs such as the kidney for diagnosing disorders in these organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the Tc-99m labeled peptide reagents are administered in a single unit injectable dose. The Tc-99m labeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The somatostatin receptor-binding cyclic peptides and non-radioactive metal complexes of the cyclic peptide reagents of the invention may be used clinically as therapeutic agents to promote regression of certain types of tumors, particularly those that express somatostatin receptors. The somatostatin analogue cyclic peptides of the invention can also be used to reduce the hormonal hypersecretion that often accompanies certain cancers, such as the APUDomas. Peptides of the invention used as therapeutic agents may be administered by any appropriate route, including intravenous, intramuscular or by mouth, and in any acceptable pharmaceutical carrier, in doses ranging from about 0.1 to about 49 mg/kg body weight/day.

This invention also provides peptides radiolabeled with cytotoxic radioisotopes such as rhenium-186 or rhenium-188 that may be used for radiotherapy of certain tumors as described above. For this purpose, an amount of radioactive isotope from about 10 mCi to about 200 mCi may be administered via any suitable clinical route, preferably by intravenous injection.

The methods for making and labeling these compounds are more fully illustrated in the following examples. These examples illustrate certain aspects of the above-described method and advantageous results, and are shown by way of illustration and not limitation.

EXAMPLE 1

Solid Phase Peptide Synthesis

Solid phase peptide synthesis (SPPS) was carried out on a 0.25 nullimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTUIHOBT), and using p-hydroxymethylphenoxy-methylpolystyrene (HMP) resin for carboxyl-terminus acids or Rink amide resin for carboxyl-terminus amides.

Where appropriate, the following amino acid derivatives were synthesized. Homocysteine was prepared by alkaline hydrolysis of L-homocysteine lactone. Threoninol residues, wherein the carboxyl group of the amino acid is reduced to a primary alcohol, can be introduced into the peptides of the invention where appropriate using the procedure of Neugebauer et al. (1990, *Peptides: Proceedings of the* 11*th American Peptide Symposium,* pp. 1020–21). Fmoc.Hcy(Trt) and Fmoc.Pen(Trt) were prepared from the appropriate amino acids by tritylation with triphenylmethanol in TFA, followed by Fmoc derivatization as described by Atherton et al. (1989, *Solid Phase Peptide Synthesis*, IRL Press: Oxford). Fmoc.homohomocysteine(Trt) was prepared by reducing NN-bis-Boc-glutamic acid-α-methyl ester with borane-THF, followed by mesylation and reaction with trityl-mercaptide, followed by removal of the Boc groups with $BF_3OEt_2$ in acetic acid, and then Fmoc derivatization as described above. phenyl-$CH_2CHBrCOOH$ was prepared by treating phenylalanine (in a solution of water and TFA/saturated with NaBr) with sodium nitrite, followed by distillation to recover the pure product.

Where appropriate, 2-chloroacetyl, 2-bromoacetyl and 2-bromo-3-phenylpropionyl groups were introduced either by using the appropriate 2-halo acid as the last residue coupled during SPPS, or by treating the N-terminus free amino acid peptide bound to the resin with either 2-halo acid/diisopropylcarbodiimide/N-hydroxysuccinimide/NMP or 2-halo acid anhydride/diisopropylethylamine/NMP.

Where appropriate, HPLC-purified 2-haloacylated peptides were cyclized by stirring an 0.1–1.0 mg/Ln solution in phosphate or bicarbonate buffer or dilute ammonium hydroxide (pH 8.0), optionally containing 0.5–1.0 mM EDTA, or acetonitrile or THF for 1–48 h followed optionally by acidification with acetic acid, lyophilization and HPLC purification.

Where appropriate, [BAM] ($N^1$,$N^4$-bis(2-mercapto-2-methylpropyl)-1,4,10-triazadecane) was conjugated to the peptide by first activating the peptide carboxylate with a mixture of diisopropylcarbodiimide/N-hydroxysuccinimide or HBTU/HOBt in DMF, NMP or methylene chloride, followed by coupling in the presence of diisopropylethylamine. After coupling, the conjugates were deprotected as described above.

Where appropriate, BSME adducts were prepared by reacting single thiol-containing peptides (5 to 50 mg/mL in DMF buffered to pH 7 with N-methylmorpholine or N-ethylmorpholine, or 50 mM sodium phosphate buffer, pH 7–8, optionally containing 0.5 mM EDTA or DMF or THF or acetonitrile) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF buffered to pH 7 with N-methylmorpholine or N-ethylmorpholine, or 5 to 50 mg/mL peptide in 50 mM sodium phosphate, pH 7–8, optionally containing 0.5 mM EDTA or DMF or THF or acetonitrile) with 0.33 molar equivalents of TMEA (tris(2-maleimidoethyl)amine) pre-dissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, BAT-BS (N-[2-(N'N'-bis(2-succinimidoethyl)aminoethyl)]-$N^6$,$N^9$-bis(2-methyl-2-mercaptopropyl)-6,9-diazanonanamide) adducts were prepared by reacting single thiol-containing peptide (at concentrations of 2 to 50 mg/mL peptide in DMF buffered to pH 7 with N-methylmorpholine or N-ethylmorpholine, or in 50 mM sodium phosphate (pH 7–8), optionally containing 0.5 mM EDTA or DMF or THF or acetonitrile) with 0.5 molar equivalents of BAT-BM (N-[2-(N',N'-bis(2-maleimidoethyl)aminoethyl)]-$N^9$-(t-butoxycarbonyl)-$N^{6,N9}$-bis(2-methyl-2-triphenylmethylthiopropyl)-6,9-diazanonanamide) pre-dissolved in acetonitrile or THF, at room temperature for approximately 1–18 h. The solution was then evaporated to dryness and [BAT-BS]-peptide conjugates deprotected by treatment with 10 mL TFA and 0.2mL triethylsilane for 1 h. The solution was concentrated, the product adducts precipitated with ether, and then purified by HPLC.

Where appropriate, the [DTPA] moiety can be introduced using the method of Bakker et al. (1991, Life Sci. 49: 1583–1591, hereby incorporated by reference).

Where appropriate, peptide precursors were cyclized (between the amino- and carboxyl-termini) by reaction of the sidechain-protected, N-terminal free amine and C-terminal free acid with diphenylphosphorylazide.

Resin-bound products were routinely cleaved using a solution of trifluoroacetic acid or trifluoroacetic acid and methylene chloride, optionally containing water, thioanisole, ethanedithiol, and triethylsilane, prepared in ratios of 100:5:5:2.5:2 for 0.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or by electrospray mass spectroscopy (ESMS).

Somatostatin analogues synthesized as provided herein, as well as the products of such synthesis identified by FABMS, are shown in Table I below.

EXAMPLE 2

A General Method for Radiolabeling with Tc-99m 0.1 mg of a peptide prepared as in Example 1 was dissolved in 0.1 mL of water or 50/50 ethanol/water or phosphate-buffered saline or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 $\mu$l of Tc-99m gluceptate was then added to the peptide and the reaction allowed to proceed at room temperature or at 100° C. for about 15–30 min and then filtered through a 0.2 $\mu$m filter.

The Tc-99m labeled peptide purity was determined by HPLC using the following conditions: a Waters Delta Pak RP-18, 5$\mu$, 4.6 mm×220 mm analytical column was loaded with each radiolabeled peptide, and the peptides eluted at a solvent flow rate equal to 1 mL/min. Gradient elution was performed beginning with 100% solvent A (0.1% $CF_3COOH/H_2O$) and ending with 100% solvent $B_{90}$ (0.1% $CF_3COOH$/90% $CH_3CN/H_2O$) over the course of 10–20 min.

Radioactive components were detected using an in-line radiometric detector linked to an integrating recorder. Tc-99m gluceptate and Tc-99m sodium pertechnetate elute between 1 and 4 minutes under these conditions, whereas the Tc-99m labeled peptides eluted after a much greater amount of time, as illustrated in Table I below.

TABLE I

| Peptide | MH + FABMS | RCY (%) | $R_t$ (min) |
|---|---|---|---|
| cyclo.(N—$CH_3$)F.$YW_D$KV.Hcy | 855 | — | — |
| $CH_2$CO.F$YW_D$KTFC.amide | 1033 | — | — |
| $CH_2$CO.F$FW_D$KTF.Hhc.amide | 1046 | — | — |
| cyclo.C$YW_D$KVC | 783 | 98[1] | 11.4[1] |
| $CH_2$CO.F$FW_D$KTFC.amide | 1017 | — | — |
| cyclo.(N—$CH_3$)F.$YW_D$,KV.K(BAT) | 1185 | 90[1] | 13.3, 14.4[1] |
| cyclo.(N—$CH_3$)F.$YW_D$KV.Hcy-($CH_2$CO.K(ε-K)GC.amide) | 1328 | nd | nd |
| cyclo.(N—$CH_3$)F.$YW_D$KV.Hcy-($CH_2$CO.$C_{Acm}$G$C_{Acm}$.amide) | 1318 | nd | nd |
| cyclo.(N—$CH_3$)F.$YW_D$KV.Hcy-($CH_2$CO.CGC.amide) | 1176 | 99[4] | 16.1[3] |
| cyclo.(N—$CH_3$)F.$YW_D$,KV.Hcy-($CH_2$CO.CGC) | 1177 | 99[4] | 15.8, 17.8[3] |
| $CH_2$CO.F$FW_D$KTFC[BAM] | 1322 | 99 | 18.8 |
| cyclo.(N—$CH_3$)F.$YW_D$KV.Hcy-($CH_2$CO.(ε-K)GC.amide) | 1201 | 99[3] | 15.3[3] |
| cyclo.(N—$CH_3$)F.$YW_D$KV.Hcy-($CH_2$CO.GGC.amide) | 1129 | 98[4] | 15.1, 17.2[3] |
| cyclo.(N—$CH_3$)F.$YW_D$KV.E(BAM) | 1171 | 98[1] | 12.3, 13.6[1] |
| $CH_2$CO.NF$FW_D$KTFTC | 1234 | — | — |
| $CH_2$CO.F$FW_D$KTFC | 1018 | — | — |
| $CH_2$CO.F$FW_D$KTFC(ε-K)GC.aimide | 1305 | 99[4] | 16.5[3] |
| $CH_2$CO.F$FW_D$KTFC$C_{Acm}$G$C_{Acm}$.amide | 1422 | 99 | 15.1–16.9 |
| $CH_2$CO.F$FW_D$KTF.Hcy | 1032 | — | — |
| $CH_2$CO.$YW_D$KTC | 740 | — | — |
| $CH_2$CO.$YW_D$KT.Hcy.amide | 768 | — | — |
| $CH_2$CO.$YW_D$KT.Hhc.T($CH_2$OH) | 855 | — | — |
| $CH_2$CO.$YW_D$KTCTGG$C_{Mob}$.amide | 1178 | — | — |
| $CH_2$CO.$YW_D$KT.Hhc | 769 | — | — |
| D-phenyl-$CH_2$CHCO.$YW_D$KTC | 830 | — | — |
| $CH_2$CO.$FW_D$KT.Pen | 752 | — | — |
| $CH_2$CO.$FW_D$KTHcy.amide | 737 | — | — |
| $CH_2$CO.$YW_D$KTCT | 841 | — | — |
| $CH_2$CO.$YW_D$KTCT($CH_2$OH) | 828 | — | — |
| $CH_2$CO.$YW_D$KTCT$C_{Acm}$G$C_{Acm}$.amide | 1246 | 94[2] | 16.6, 16.9[2] |
| $CH_2$CO.$FW_D$KTHcy | 738 | — | — |
| $CH_2$CO.$YW_D$KTC.amide | 740 | — | — |

* The following labeling conditions were used with the appropriate peptides:
[1]The peptide is dissolved in water and labeled at room temperature.
[2]The peptide is dissolved in water and labeled at 100 • C. (15 min).
[3]The peptide is dissolved in 10% hydroxypropylcyclodextrin and labeled at room temperature.
[4]The peptide is dissolved in 50% ethanol/water and labeled at room temperature.
** HPLC methods:
general:
solvent A = 0.1% CF3COOH/$H_2O$
solvent $B_{90}$ = 0.1 % $CF_3COOH$/90% $CH_3CN/H_2O$
solvent flow rate = 1 mL/min
Vydak column = Vydak 218TP54 RP-18, 5 • × 220 mm × 4.6 mm analytical column with guard column
Waters column = Waters Delta-Pak C18, 5 • m, 39 × 150 mm
Method 1: Waters column 100% A to 100% $B_{90}$ in 10 min
Method 2: Vydak column 100% A to 100% $B_{90}$ in 10 min
Method 3: Waters column 100% A to 100% $B_{90}$ in 20 min
Abbreviations are as set forth above. In addition, BAT acid (protected) = $N^9$-(t-butoxycarbonyl)-$N^6$,$N^9$-bis(2-methyl-2-triphenylmethylthiopropyl)-6, 9-diazanonanoic acid; BAM (protected) = $N^1$-(t-butoxycarbonyl)-$N^1$,$N^4$-bis (2-methyl-2-triphenylmethylthiopropyl)-1,4,10-triazadecane.

EXAMPLE 3

Inhibition of Binding of [$^{125}$I-Tyr$^{11}$]somatostatin-14 to AR42J Rat Pancreatic Tumor Cell Membranes The ability of various somatostatin analogues of the invention to bind to somatostatin receptors in vitro was demonstrated by assaying the ability of such analogues to inhibit binding of a radiolabeled somatostatin analogue to somatostatin receptor-containing cell membranes. The rat pancreatic tumor cell line AR42J which expresses the somatostatin receptor was cultured in Dulbecco's minimal essential media (DMEM) supplemented with 10% fetal bovine serum (FBS) and 8mM glutamine in a humidified 5% $CO_2$ atmosphere at 37° C. in T-flasks. Harvested cells were homogenized in cold 50 mM Tris-HCl buffer (pH 7.4) and the homogenate then centrifuged at 39,000 g for 10 min at 4° C. Pellets were washed once with buffer and then resuspended in an ice-cold solution of 10 mM Tris-HCl (pH 7.4). Equal aliquots of this cell membrane preparation were incubated with [$^{125}$I-Tyr$^{11}$]somatostatin-14 (at a final concentration of 0.5 nM and 750,000 cpm/mL, at a specific activity of 2000 Ci/mmol, Amersham, Arlington Heights, Ill.) and peptide or peptide-rhenium complex at a final concentration of from $10^{-11}$M to $10^{-6}$M in a solution of 50 mM HEPES (pH 7.4) containing 1% bovine serum albumin (BSA), 5 mM $MgCl_2$, Trasylol (200,000 International Units), bacitracin (0.02 mg/mL) and phenylmethylsulfonylfluoride (0.02 mg/mL) for 25 min at 30° C. Using a filtration manifold, this mixture was filtered through a polyethyleneimine-washed GC/F filter (Whatman, Maidstone, England), and the residue remaining on the filter washed thrice with 5 mL cold HEPES buffer. The filter and a sample of the filter washings were then counted in a gamma counter. To assess non-specific binding, the assay was performed in the presence of unlabeled somatostatin-14 at 200 nM. Data analysis including Hill plots of the data provided inhibition constants (see Bylund & Yamamura, "Methods of receptor binding", in *Methods in Neurotransmitter Receptor Analysis*, Yamamura et al., eds., Raven Press: New York, 1990).

These results are presented in the following Tables. The data show that the peptides of the instant invention have a high affinity of binding for somatostatin receptors.

TABLE II

| [Re = O]-complexed Peptides | $MH^+$ | $K_i$ (nM) |
|---|---|---|
| cyclo.(N—$CH_3$)F.$YW_D$KV.Hcy-($CH_2$CO.K(ε-K)GC.amide) | 1529 | 0.51 |
| cyclo.(N—$CH_3$)F.$YW_D$KV.Hcy-($CH_2$CO.GGC.amide) | 1330 | 0.59 |
| $CH_2$CO.F$FW_D$KTFC$C_{Acm}$.amide | 1480 | 0.67 |
| cyclo.(N—$CH_3$)F.$YW_D$KV.Hcy-($CH_2$CO.(ε-K)GC.amide) | 1401 | 0.92 |
| cyclo.(N—$CH_3$)F.$YW_D$KV.Hcy-($CH_2$CO.CGC.amide) | 1375 | 1.7 |
| $CH_2$CO.F$FW_D$KTFC(ε-K)GC | 1506 | 5.9 |

TABLE III

| Peptide | $K_i$ (nM) |
|---|---|
| cyclo.(N—$CH_3$)F.$YW_D$KV.Hcy | <0.01 |
| $CH_2$CO.F$YW_D$KTFC.amide | 0.16 |

TABLE III-continued

| Peptide | $K_i$ (nM) |
|---|---|
| $CH_2CO.FFW_DKTF.Hhc.amide$ | 0.41 |
| $cyclo.CYW_DKVC$ | 0.43 |
| $CH_2CO.FFW_DKTFC.amide$ | 0.45 |
| cyclo.(N—$CH_3$)F.$YW_DKV.K$.[BAT] | 0.46 |
| cyclo.(N—$CH_3$)F.$YW_DKV$.Hcy-($CH_2CO$.K(ε-K)GC.amide) | 0.65 |
| cyclo.(N—$CH_3$)F.$YW_DKV$.Hcy-($CH_2COC._{Acm}GC_{Acm}$.amide) | 0.79 |
| cyclo.(N—$CH_3$)F.$YW_DKV$.Hcy-($CH_2CO$.CGC.amide) | 1.5 |
| cyclo.(N—$CH_3$)F.$YW_DKV$.Hcy-($CH_2CO$.CGC) | 1.8 |
| $CH_2CO.FFW_DKTFC$.[BAM] | 1.9 |
| cyclo.(N—$CH_3$)F.$YW_DKV$.Hcy-($CH_2CO$.(ε-K)GC.amide) | 2.0 |
| cyclo.(N—$CH_3$)F.$YW_DKV$.Hcy-($CH_2CO$.GGC.amide) | 2.4 |
| cyclo.(N—$CH_3$)F.$YW_DKV$.E.[BAM] | 2.6 |
| $CH_2CO.NFFW_DKTFTC$ | 2.7 |
| $CH_2CO.FFW_DKTFC$ | 4.0 |
| $CH_2CO.FFW_DKTFC$(ε-K)GC.amide | 5.2 |
| $CH_2CO.FFW_DKTFCC_{Acm}GC_{Acm}$.amide | 7.5 |
| $CH_2CO.FFW_DKTF$.Hcy | 9.8 |

It should be understood that the foregoing disclosure emphasizes certain specific embodiments of the invention and that all modifications or alternatives equivalent thereto are within the spirit and scope of the invention as set forth in the appended claims.

What is claimed is:

1. A somatostatin receptor-binding peptide having a formula:

cyclo-$A^4$-$B^1B^2B^3B^4$-$C^4$- wherein $B^1$ is D- or L-Phe or D- or L-Tyr or D- or L-Nal or Ain;

$B^2$ is D- or L-Trp;

$B^3$ is D- or L-Lys or Hly, Achxa, Amf, Aec, Apc, Aes, or Aps;

$B^4$ is Thr, Ser, Val, Phe, Ile, Abu, Nle, Leu, Nva or Aib;

$C^4$ is an L-amino acid having a sidechain comprising a mercapto group;

$A^4$ is a lipophilic D-amino acid or a lipophilic L-(α-N-alkyl)amino acid or L-proline;

wherein $A^4$ and $C^4$ are covalently linked through an amino terminus of $A^4$ and a carboxyl terminus of $C^4$.

2. The peptide of claim 1, wherein $B^1$ is phenylalanine or tyrosine, $B^2$ is D-tryptophan, $B^3$ is lysine and $B^4$ is threonine or valine.

3. The peptide of claim 1, further comprising a radioisotope selected from the group consisting of iodine-123, iodine-125, iodine-131, and astatine-211.

4. A multimer having a molecular weight of less than about 20,000 daltons comprising:

a) at least two somatostatin receptor-binding peptides, each having a formula:

cyclo-$A^4$-$B^1B^2B^3B^4$-$C^4$- wherein $B^1$ is D- or L-Phe or D- or L-Tyr or D- or L-Nal or Ain;

$B^2$ is D- or L-Trp;

$B^3$ is D- or L-Lys or Hly, Achxa, Amf, Aec, Apc, Aes, or Aps;

$B^4$ is Thr, Ser, Val, Phe, Ile, Abu, Nle, Leu, Nva or Aib;

$C^4$ is an L-amino acid having a sidechain comprising a mercapto group;

$A^4$ is a lipophilic D-amino acid or a lipophilic L-(α-N-alkyl)amino acid or L-proline;

wherein $A^4$ and $C^4$ are covalently linked through an amino terminus of $A^4$ and a carboxyl terminus of $C^4$; and b) a polyvalent linker covalently linked to each peptide.

5. The multimer of claim 4, wherein the linker is selected from the group consisting of bis-succinimidylmethylether, 4-(2,2-dimethylacetyl)benzoic acid, N-[2-(N',N'-bis(2-succinimidoethyl)aminoethyl)]-$N^6$,$N^9$-bis(2-methyl-2-mercaptopropyl)-6,9-diazanonanamide, tris (succinimidylethyl)amine, bis-succinimidohexane, and 4-(O—$CH_2$CO-Gly-Gly-Cys.amide)-2-methylpropiophenone.

6. A kit for preparing a radiopharmaceutical preparation, said kit comprising a sealed vial containing a predetermined quantity of the peptide of claim 1.

* * * * *